United States Patent [19]
Nowicki et al.

[11] Patent Number: 5,824,480
[45] Date of Patent: Oct. 20, 1998

[54] METHOD OF DIFFERENTIATING PELVIC INFLAMATORY DISEASE AND LOCAL ISOLATES OF *NEISSERIA GONORRHOEAE*

[75] Inventors: Stella Nowicki; Bogdan Nowicki; Garland D. Anderson, all of Galveston, Tex.

[73] Assignee: The Board of Regents of the University of Texas System, Austin, Tex.

[21] Appl. No.: 644,426

[22] Filed: May 10, 1996

[51] Int. Cl.$^6$ .............................. C12Q 1/68; C12P 19/34; C07H 21/04

[52] U.S. Cl. .............................. 435/6; 435/912; 536/23.1; 536/23.7; 536/24.32; 536/24.33; 935/6; 935/77; 935/78

[58] Field of Search .................................. 536/23.1, 23.7, 536/24.33, 24.32; 935/6, 77, 78; 435/6, 91.2, 75

[56] References Cited

PUBLICATIONS

Rice et al. The Journal of Immunology 124:2105–2109 (May 1980).

*Primary Examiner*—W. Gary Jones
*Assistant Examiner*—Debra Shoemaker
*Attorney, Agent, or Firm*—Benjamin Aaron Adler

[57] ABSTRACT

The present invention provides a method of differentially diagnosing pelvic inflammatory disease from local infection of *Neisseria gonorrhoeae* in an individual, comprising the step of identifying whether the individual carries a strain of *Neisseria gonorrhoeae* which is stable resistant to the bacteriocidal effects of normal human serum. Also provided is a method of differentially diagnosing pelvic inflammatory disease from local infection of *Neisseria gonorrhoeae* in an individual, comprising the step of determining the presence of a 344 base pair DNA sequence from the 2.2 kb sac-4 region of *Neisseria gonorrhoeae* in a clinical isolate obtained from said individual.

6 Claims, 2 Drawing Sheets

```
5'TATCTGCAGC ATCTCCTTTC CAACCCAATT TTCCTTTGTC

ACCAATAAAA CTTTGCATAT TTCTAGCCAT TTCTCCAATG

GTACCAGCAC TTTTAGAAAG ACTTTCTAAT CCCTGCGCTC

CTTTTTGAAT CATAGTTTGA GCTAATCTCG TAGATGCAGA

TTTCTTTTCA GATGCTGTTT CACTTCCGCC TGCACCAGT

CCTATTGCAA TGGCAGAGGC AATAGAAGAA GCATTGCTGA

TATTAAATTG TTGGCCAATC TTCTTACCTC GATCAAGAAC

GTAAGATAAT TTCTACTTT CAGCTGCATC CAAACCCATT

CCGTAACCTT CAGAGGCACT TCTA 3'
```

```
5'TATCTGCAGC ATCTCCTTTC CAACCCAATT TTCCTTTGTC
  ACCAATAAAA CTTTGCATAT TTCTAGCCAT TTCTCCAATG
  GTACCAGCAC TTTTAGAAAG ACTTTCTAAT CCCTGCGCTC
  CTTTTTGAAT CATAGTTTGA GCTAATCTCG TAGATGCAGA
  TTTCTTTTCA GATGCTGTTT CACTTCCGCC TGCACCAGT
  CCTATTGCAA TGGCAGAGGC AATAGAAGAA GCATTGCTGA
  TATTAAATTG TTGGCCAATC TTCTTACCTC GATCAAGAAC
  GTAAGATAAT TTTCTACTTT CAGCTGCATC CAAACCCATT
  CCGTAACCTT CAGAGGCACT TCTA 3'
```

FIGURE 2

METHOD OF DIFFERENTIATING PELVIC INFLAMATORY DISEASE AND LOCAL ISOLATES OF *NEISSERIA GONORRHOEAE*

BACKGROUND OF THE INVENTION

1. Field of the Invention

The present invention relates generally to the fields of biochemistry, gynecology and molecular biology. More specifically, the present invention relates to a method of differentiating pelvic inflammatory disease and local isolates of *Neisseria gonorrhoeae*.

2. Description of the Related Art

Of the sexually transmitted diseases that affect women, gonococcal pelvic inflammatory disease (PID) is among the most serious and costly (*Sex Trans Dis.* 1:46–64, 1991). The cost of treating pelvic inflammatory disease in the U.S. has been estimated to reach $10 billion by the year 2000 (*Sex Trans Dis.* 1:46–64, (1991)). Pelvic inflammatory disease frequently results in severe, irreversible sequelae such as infertility, ectopic pregnancy and chronic pelvic pain (*Sex Trans Dis.* 1:46–64, 1991), (Rice et al., *JAMA* 266:2587–2593, 1991), (US Govt. Sex Trans Dis. In: *DHHS & Pub Health Serv., Natl Health Pro & Dis Prev. Obj.* Healthy People 2000, Washington, DC; 496–508, 1991), (Morse et al. *Infec. Dis.* 1:639–656, 1989). Unfortunately, there is no objective diagnostic method available to identify patients at risk for pelvic inflammatory disease. Clarification whether development of gonococcal pelvic inflammatory disease is determined by the host susceptibility or by the virulence of the gonococcus would significantly contribute to improvement of diagnostic, therapeutic and prophylactic approaches.

*Neisseria gonorrhoeae* is a frequent cause of sexually transmitted disease in the United States and worldwide. One to three percent of gonococcal infections may result in a severe life threatening complication generally referred to as disseminating gonococcal infection (DGI). Virulence and resistance to the complement dependent bactericidal effect of normal human serum appear to be closely associated for this gram negative diplococcus. Spink & Keefer reported in 1937 that gonococci isolated from uncomplicated genital infections were killed more efficiently by fresh defibrinated blood from healthy male volunteers than isolates from systemic infections. Schoolnik et al. first demonstrated that strains from disseminating gonococcal infection were serum resistant while strains from uncomplicated infection were sensitive to the lytic effect of normal human serum. Glynn & Ward showed that some strains of gonococci were resistant to the bactericidal effect of normal human serum but after subculture become serum sensitive ($Ser^s$). Serum resistance of gonococci isolated from cervical cultures range from fully serum resistant to fully serum sensitive, with some intermediate degrees of serum resistance and the phenotype is associated with clinical complications manifesting mainly during menstruation.

Serum resistance phenotype in *N. gonorrhoeae* seems to be under polygenic control. A locus close to but distinct from the one coding for protein I termed Sac-1 was shown by Canon et al. to determine serum resistance. Subsequently, Shafer et al. described a Sac-3 locus on the gonococcal chromosome which upon linking to Sac-1 increased the serum resistance of this organism. McShan et al. described in 1989 a 2.2 kb region on the gonococcal DNA, called sac-4. Upon transformation to serum sensitive strain F62, the resulting recombinant strain WM3 turned serum resistant. A part of the sac-4 region from serum resist donor JC1 was cloned, but a DNA segment of sac-4 common for other serum resistant clinical isolates was not identified. Identification of a DNA segment that would characterize stable serum resistant isolates would contribute to the generation of a simple reliable diagnostic test to detect serum resistance and thereby detect highly virulent strains associated with bacteremia.

The prior art is deficient in the lack of an effective method of differentiating pelvic inflammatory disease and local isolates of *Neisseria gonorrhoeae* and the lack of a simple reliable diagnostic test to detect stable serum resistance and thereby detect highly virulent strains associated with bacteremia. The present invention fulfills this longstanding need and desire in the art.

SUMMARY OF THE INVENTION

One object of the present invention is to provide a method of differentiating pelvic inflammatory disease and local isolates of *Neisseria gonorrhoeae* in an individual in need of such diagnosis.

Another object of the present invention is to provide a simple reliable diagnostic test to detect stable serum resistance and thereby detect highly virulent strains associated with bacteremia.

The present invention demonstrates that a 344 base pair DNA fragment is present in clinical gonococcal isolates which are resistant to the bactericidal effect of normal human serum. A serum assay with normal human serum was carried out to confirm the serum susceptibility of clinical isolates (obtained from the Centers for Disease Control, Atlanta and from University of Texas-Medical Branch clinics). Primers designed for the 344 base pair DNA segment were used and a polymerase chain reaction (PCR) was carried out using the lysates of the various gonococcal isolates. A serum assay was then carried out with these strains using 50% of normal human serum and the percentage survival of these strains was studied. Twenty gonococcal strains were studied. Ten strains were positive on PCR and of this nine were resistant to the action of normal human serum. Ten strains gave a negative result with PCR and nine of these strains were serum sensitive.

The present invention demonstrates that clinical gonococcal pelvic inflammatory disease isolates which tested positive for this 344 base pair DNA segment were serum resistant while local infection strains which lacked this fragment were serum sensitive. Thus, the present invention provides a person having ordinary skill in this art with the knowledge which allows the identification of serum resistant clinical pelvic inflammatory disease gonococcal strains based on the presence of this 344 base pair DNA segment of sac-4. Characterization of this region allows development of various diagnostic measures against severe gonococcal infections.

In one embodiment of the present invention, there is provided a method of differentially diagnosing pelvic inflammatory disease from local infection of *Neisseria gonorrhoeae* in an individual, comprising the step of identifying whether the individual carries a strain of *Neisseria gonorrhoeae* which is stable resistant to the bacteriocidal effects of normal human serum.

In another embodiment of the present invention, there is provided a method of differentially diagnosing pelvic inflammatory disease from local infection of *Neisseria gonorrhoeae* in an individual, comprising the step of determining the presence of a 344 base pair DNA sequence from the 2.2 kb sac-4 region of the *Neisseria gonorrhoeae* JC1 strain in a clinical isolate obtained from said individual.

In yet another embodiment of the present invention, there is provided a diagnostic kit for use in differentially diagnosing pelvic inflammatory disease from local infection of *Neisseria gonorrhoeae* in an individual, said kit comprising (a) primers for 344 base pair DNA sequence from the 2.2 kb sac-4 region of the *Neisseria gonorrhoeae* JC1 strain, (b) means for detecting and measuring the binding of the primers to said fragment.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows sequence of the 344 base pair DNA segment of sac-4 used in the methods of the present invention SEQ ID No. 3.

DETAILED DESCRIPTION OF THE INVENTION

Figure 1:
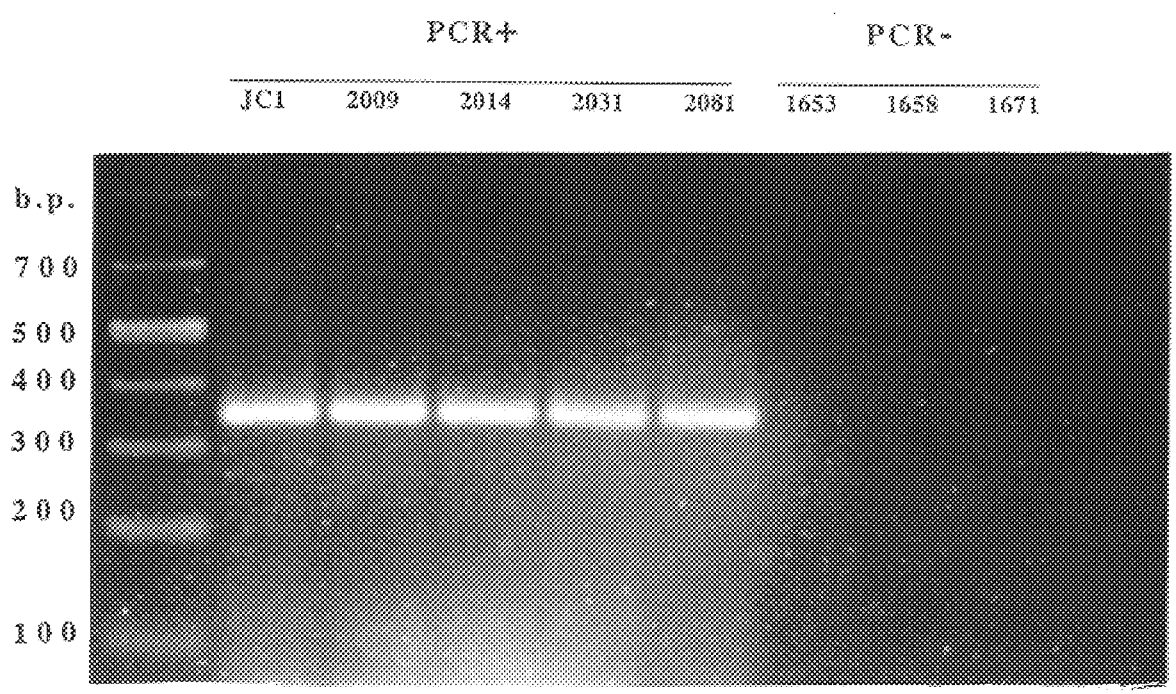
FIG. 1 shows the amplification of the 344 bp fragment by PCR of GC strains indicating its presence in strains causing gonococcal pelvic inflammatory disease (PID) and disseminated gonococcal infection (DGI). The fragment is absent in GC strains from local infection. JC1-DCI strain 2009, 2014, 2037, 2081—PID strains; 1653, 1658, 1671—local gonococcal isolates. The left side of graph shows the base pair scale.

The present invention is directed to a method of differentially diagnosing pelvic inflammatory disease from local infection of *Neisseria gonorrhoeae* in an individual, comprising the step of identifying whether the individual carries a strain of *Neisseria gonorrhoeae* which is stably resistant to the bacteriocidal effects of normal human serum.

The present invention is also directed to a method of differentially diagnosing pelvic inflammatory disease from local infection of *Neisseria gonorrhoeae* in an individual, comprising the step of determining the presence of a 344 base pair DNA sequence from the 2.2 kb sac-4 region of the *Neisseria gonorrhoeae* JC1 strain in a clinical isolate obtained from said individual. Preferably, the 344 base pair DNA sequence is determined using a polymerase chain reaction. More specifically, the 344 base pair DNA has the sequence shown in SEQ ID No. 3. In one embodiment, a person having ordinary skill in this art may use, in such a polymerase chain reaction, the primers shown in SEQ ID Nos. 1 and 2. Clearly, a person having ordinary skill in this art would readily recognize that other primers may be prepared which will bind to and allow detection of the 344 base pair DNA sequence, the presence of said 344 base pair DNA sequence correlates positively with a stable serum resistance phenotype.

The present invention is also directed to a diagnostic kit for use in differentially diagnosing pelvic inflammatory disease from local infection of *Neisseria gonorrhoeae* in an individual, said kit comprising (a) primers for 344 base pair DNA sequence from the 2.2 kb sac-4 region of the *Neisseria gonorrhoeae* JC1 strain; and (b) means for detecting and measuring the binding of the primers to said fragment. A person having ordinary skill in this art would readily recognize that are various detection means in the art such as PCR, etc. to determine the presence of the 344 base pair fragment. In one embodiment, the kit contains the primers have the sequence shown in SEQ ID Nos. 1 and 2.

The following examples are given for the purpose of illustrating various embodiments of the invention and are not meant to limit the present invention in any fashion.

EXAMPLE 1

Virulence of pelvic inflammatory disease strains differ from local isolates and can be estimated, as demonstrated by the present invention, on the recently developed newborn rat model. In this nonhuman host, gonococcal infection was achieved with the use of human complement C1q. To demonstrate this, 18 pelvic inflammatory disease and 14 local isolates of *N. gonorrhoeae* collected at the Centers for Disease Control and Prevention were tested for C1q-dependent virulence in newborn rats. Groups of five-day-old rats received intraperitoneal inoculation (i.p.) of 100 $\mu$l of 5 $\times 10^6$ gonococci and human complement C1q (100 $\mu$g/ml). The control animals received 100 ml of $5 \times 10^6$ gonnococci and bovine serum albumin (BSA) (100 $\mu$g/ml). At 4 hours post-inoculation, blood from each rat (No. 340) was cultured. Of the 32 strains preincubated with C1q, 16 were recovered from the blood of rat pups. Of the 16 gonococcal strains, 14 (77%) were obtained from patients with pelvic inflammatory disease and 2 (14%) from local infection. Cultures from control animals (No. 160) inoculated with 32 strains in bovine serum albumin were negative.

The auxotype and/or serovar of the strains did not correlate with virulence of gonococci in newborn rats or the clinical type of infection (TABLE I). Thus, the present invention demonstrates that the C1q-dependent virulence of gonococci in the rat pup seems to be the first phenotype, which differentiates pelvic inflammatory disease from local isolates. Such a classification showed high correlation with clinical diagnosis of gonococcal pelvic inflammatory disease.

TABLE I

Characterization of gonococcal clinical isolates based on an animal model

| Clinical type of infection | PID | Local |
|---|---|---|
| No. of strains | 18 | 14 |
| Virulent to rat pups No./(%) | 14(77%)* | 2(14%) |
| Dominating Auxotype No./(%) | Proto 7(37%) | Proto 5(35%) |
| Dominating Serovar No./(%) | 1B3 4(22%) | 1B4 2(14%) |

*p $\leq$ 0.001; % of positive blood culture

Thus, the present invention demonstrates that development of pelvic inflammatory disease is determined by the specific virulence of the gonococcus and is directed by the ability of gonococci to use the specific host factor C1q. Fourteen percent of the local isolates that were classified as virulent in rat pups reflect those patients which are in early stage of local gonococcal infection and who are at risk of developing pelvic inflammatory disease. This value is similar to the proportion of women with local gonococcal infection who later develop pelvic inflammatory disease (15–25%) (Morse et al., *Infect. Dis.* 1:639–656, 1989). Thus, the identification of these strains in an early stage of infection, as now provided by the present invention, would reduce the number of patients with serious complications (*Sex Trans Dis.* 1:46–64, 1991), (US Govt. Sex Trans Dis. In: *DHHS & Pub Health Serv. Natl Health Pro & Dis Prev. Obj.*, Healthy People 2000, Washington, DC 496–508, 1991), (Morse et al. *Infect. Dis.* 1:639–656, 1989), and will significantly decrease the economic burden of pelvic inflammatory disease.

EXAMPLE 2

*Neisseria gonorrhea* is an important cause of sexually transmitted disease in the United States. The incidence of gonococcal infections has shown a sharp increase in the teenage population over the past decade. One of the important factors contributing to the virulence of gonococci is its resistance to the bactericidal effect of normal human serum. A 344 base pair segment in the 3' end of the sac-4 region which confers serum resistance to serum sensitive strain F62 upon transformation with plasmid pRP350 has recently been identified.

The present invention demonstrates that a polymerase chain reaction (PCR) assay can be used to detect that a specific segment of the sac-4 region is amplified from the genomic DNA of the clinical strain and correlates specifically with the stable serum resistance phenotype.

EXAMPLE 3
Bacterial strains

All gonococcal strains were obtained from Communicable Disease Center (Atlanta) to ensure a representative collection of strains from across the United States. All strains were grown on Chocolate or Modified Thayer Martin agar (Remel laboratories). Plate cultures were incubated at 37° C. in 5% $CO_2$. Liquid cultures were grown in gonococcal base broth (GCBB), supplemented with 1% supplement VX, 0.04% sodium bicarbonate, and 5 g of glucose per liter.

EXAMPLE 4
Polymerase Chain Reaction (PCR)

PCR was used to amplify the 344 base pair fragment of DNA from the sac-4 region. Overnight, 1 ml gonococcal base broth cultures of gonococci was centrifuged and resuspended in 200 ml of $H_2O$. The samples were boiled at 100° C. for 20 minutes. Following a 5 minute micro centrifugation of the lysates, the supernatants were removed and stored at −20° C. for use as PCR templates. Primers were designed to detect the 344 base pair fragment of the 2.2 kb sac-4 of gonococcal. The sequence of the primers is:

Primer A- 5' TATCTGCAGCATCTCCTTTCCAACC 3'SEQ ID No. 1; and

Primer B- 5' TAGGAATTCCTCTGAAGGTTACGG 3'SEQ ID No. 2

PCR was done using Gene Amp PCR reagent kit (Perkin Elmer Cetus). The reaction mixture consisted of 2 µl of DNA template, 200 mM of each deoxynucleotide phosphate, 2.5 units of amplitaq polymerase and 1.0 mM each primer to a total volume of 100 µl. The reaction mixture was overlaid with 50 µl of mineral oil. The amplification reaction consisted of 30 cycles of one minute denaturation at 92° C., one minute annealing at 55° C. and 1 minute extension at 72° C. An aliquot of 20 µl from each tube was removed for analysis of 2% agarose gel.

EXAMPLE 5
Serum bactericidal resistance assay

The serum bactericidal resistance assay used was a modification of the procedure used by McCutchan et al (12). Gonococci (P+ Op+) was removed from an overnight gonococcal base broth plate culture with a sterile dacron swab and suspended in gonococcal base broth to an $A_{600}$ of 0.2. A 1:1,000 dilution was made, and 0.1 ml of the gonococcal dilution was combined with 0.1 ml of normal human serum (Sigma). This mixture was incubated for 1 hour 37° C. To another 0.1 ml sample of the gonococcal dilution 0.1 ml of heated human serum (HHS) (at 56° C. for 30 minutes) was added and incubated at 37° C. for 1 hour. There was no effect on the viability of the strains when gonococcal base broth was substituted for heated human serum (data not shown). At the end of the incubation period, 10-fold and 100-fold dilutions were made from the assay mixture, and 0.05 ml portions were spread on gonococcal base broth plates. The plates were incubated for 24 hours at 37° C. in a $CO_2$ incubator and the numbers of colony forming units (CFU) were determined.

EXAMPLE 6
Effect of normal human serum on the clinical isolates

To show the resistance to the bactericidal capacity of normal human serum exhibited by these clinical isolates, the bacteria surviving as CFU when a defined amount of bacteria was taken and subjected to complement enriched human serum at a 50% concentration was determined. Greater than 90% killing in normal human serum as compared to the survival in broth was taken as a strain being serum sensitive. Ten clinical strains stable serum resistant and 10 strains serum sensitive were selected for PCR assay (TABLES II AND III).

To understand why some serum resistant strains have increased virulence during menstruation, the survival of serum resistance in normal human serum (as a component of blood) in longer term time than in classical serum assay (30 minutes) was analyzed. Strains of *N. gonorrhoeae* tested in 50% normal human serum showed different pattern of serum resistance, from fully serum resistant (100% survival) to partially serum resistance (50% survival to 25% survival).

Lower percent survival may suggest that the bacteria were more slowly killed in normal human serum and that exposure to 50% of normal human serum for longer than 30 minutes may eliminate the rest of bacteria that ordinarily would survive in normal human serum after 30 minutes. Therefore, selected strains representing each group were retested for survival in normal human serum for longer periods of time, for example, 45 minutes, 90 minutes and 180 minutes. Results of these experiments showed that full serum resistance after 90 minute exposure to normal human serum not only survived in 100% but the number of CFU/ml increased to 200%. After the next 90 minutes, the number of CFU/ml even increased to 300% from point 0 or when compared with control exposed to gonococcal broth after the same time.

Strains which survived in 70% to 50% in normal human serum after 45 minute exposure to normal human serum showed different pattern of survival in time. After 90 minutes and for the next 90 minutes, the number of CFU did not change. Strains of *N. gonorrhoeae* representing the group with a lower percent survival between 30% to 20% were not killed progressively in time. It is not clear if nonpathogenic Neisseria strains are serum sensitive or resistant. Therefore, this was determined using a serum assay.

Two nonpathogenic strains of *Neisseria cineria* and *Neisseria flavescens* should be fully serum sensitive in 50% of normal human serum. Even 25% of normal human serum kill nonpathogenic Neisseria after 30 minutes.

EXAMPLE 7
PCR

Molecular analysis of the 2.2 kb sac-4 region of JC1 led to the identification of a smaller 344 base pair DNA segment that conferred serum resistance to *N. gonorrhoeae* F62 (FIG. 2). To demonstrate the contribution of the 344 base pair DNA segment of sac-4 in the pathogenesis of gonococcal infection, all 20 strains of *N. gonorrhoeae* and two non-pathogenic Neisseria strains were analyzed by PCR for presence of the 344 base pair segment in DNA. To demonstrate the association of the 344 base pair DNA segment with a stable serum resistant phenotype in clinical isolates, primers were designed to amplify a 344 base pair segment in the 3' end of sac-4 region and a polymerase chain reaction was performed (FIG. 1). It was observed that 10 strains of *N. gonorrhoeae* were positive on the PCR assay, while 10 strains were negative after PCR analysis. Of the 10 strains which were positive, 9 strains were serum resistant. Of the 10 strains which gave a negative reaction on PCR, 9 were serum sensitive. One strain of the 20 clinical isolates was PCR negative but serum resistant and one strain was serum sensitive, PCR positive (TABLES II AND III).

TABLE II

PCR pattern of stable serum resistant clinical strains

| | PCR | SURVIVAL IN SERUM | AUXOTYPE | SEROTYPE |
|---|---|---|---|---|
| 2004 | + | +++ | Pro | 1A6 |
| 2005 | + | + | Pro | 1B3 |
| 2081 | + | +++ | Pro | 1B7 |
| 2075 | + | +++ | Arg | 1B6 |
| 2014 | + | ++++ | Arg | 1B3 |
| 2086 | + | +++ | Arg | 1B6 |
| 2009 | + | ++ | Proto | 1B6 |
| 2015 | + | + | Proto | 1B3 |
| 1663 | − | + | Proto | 1B3 |
| 2037 | + | ++++ | Proto | 1B3 |
| 2065 | + | ++ | Proto | 1B3 |

*(10% or less survival in comparison with broth taken as negative).
+90% or more killing in 50% of normal human serum in comparison with GC broth taken as serum sensitive.

TABLE III

PCR pattern of serum sensitive clinical strains

| | PCR | SURVIVAL IN NHS | AUXOTYPE | SEROTYPE |
|---|---|---|---|---|
| 1653 | − | − | Pro | 1B4 |
| 1657 | − | − | Pro | 1B1 |
| 2016 | − | − | Pro | 1B14 |
| 2019 | − | − | Pro | 1B1 |
| 1671 | − | − | Pro | 1B2 |
| 1659 | + | − | Arg | 1A1 |
| 1673 | − | − | Proto | NT |
| 1658 | − | − | Proto | 1B4 |
| 1660 | − | − | Proto | 1B2 |

*10% or less survival in comparison with GC broth taken as $ser^s$ and marked as (−) negative.

EXAMPLE 8

Serotyping and Auxotyping

Serotyping and auxotyping was performed to see if there was any correlation between the serotypes and auxotypes and the presence of serum resistance. The various serotypes and auxotypes have been listed in TABLES II AND III. There was no observable correlation between the auxotypes and serotypes and serum resistance phenotype in these clinical strains. There was also no observable correlation between PCR positivity and the serotype and auxotype of these strains.

Discussion

Serum resistance has been attributed as an important factor in the virulence of *N. gonorrhoeae* (12). It has been shown that strains from disseminating gonococcal infection were resistant to the lytic effect of human sera while strains from uncomplicated infection were killed by the action of human serum (13).

Various reports have shown that the serum resistance property of *N. gonorrhoeae* is a general property of isolates from disseminating, invasive and complicated gonococcal infections (11,14). Previous analysis of various pathogenic and nonpathogenic Neisserial strains using a part of sac-4 DNA as a probe was not able to differentiate between pathogenic Neisserial strains (Conde-Glez J., et al., 6th Inter. Path. Neisseria Conf., 1988).

In the present invention, a reduced fragment of sac-4 described by McShan was utilized to further characterize the various clinical strains. It was demonstrated that strains which possess the 344 base pair DNA fragment in the 3' end of sac-4 were stable serum resistant while strains which lacked this segment of 2.2 kb DNA were serum sensitive. Over 90% of the strains which were serum resistant gave a positive reaction on PCR for the 344 base pair DNA segment while only 10% of serum sensitive strains were positive on PCR. Thus, a correlation between the presence of the 344 base pair DNA segment and the property of serum resistance exhibited by clinical isolates of *N. gonorrhoeae* can to be drawn.

Serotyping and auxotyping of these strains demonstrated that serum resistance and hence virulence was not confined to any specific serotype or auxotype. Thus, in the present invention, an association was experimentally demonstrated for the first time between the presence of certain DNA segments and the property of serum resistance. The present invention also provides a person having ordinary skill in this art with sufficient information to clinically apply this knowledge to identify serum resistant strains and hence allow early detection of patients susceptible to complicated gonococcal infections like dissemination.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of differentially diagnosing pelvic inflammatory disease from local infection of *Neisseria gonorrhoeae* in an individual, comprising the step of determining the presence of a 344 base pair DNA sequence from the 2.2 kb sac-4 region of the *Neisseria gonorrhoeae* JC1 strain in a clinical isolate obtained from said individual, and, wherein said 344 base pair DNA has the sequence of SEQ ID No. 3 and wherein the presence of said 344 base pair DNA sequence is indicative of pelvic inflammatory disease.

2. The method of claim 1, wherein said 344 base pair DNA sequence is determined using a polymerase chain reaction.

3. The method of claim 2, wherein said polymerase chain reaction uses the primers on SEQ ID Nos. 1 and 2.

4. The method of claim 1, wherein the presence of said 344 base pair DNA sequence correlates positively with a stable serum resistance phenotype.

5. A diagnostic kit for use in differentially diagnosing pelvic inflammatory disease from local infection of *Neisseria gonorrhoeae* in an individual, said kit comprising
   (a) primers for the 344 base pair DNA sequence from the 2.2 kb sac-4 region of the *Neisseria gonorrhoeae* JC1 strain, wherein said 344 base pair DNA has the sequence shown in SEQ ID No. 3;
   (b) means for detecting and measuring the binding of the primers to said DNA sequence.

6. The kit of claim 5, wherein said primers have the sequence of SEQ ID Nos. 1 and 2.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:1:

TATCTGCAGC ATCTCCTTTC CAACC        25

( 2 ) INFORMATION FOR SEQ ID NO:2:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:2:

TAGGAATTCC TCTGAAGGTT ACGG        24

( 2 ) INFORMATION FOR SEQ ID NO:3:

( i ) SEQUENCE CHARACTERISTICS:
        ( A ) LENGTH: 344
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

(B) STRAIN:
(C) INDIVIDUAL ISOLATE:
(D) DEVELOPMENTAL STAGE:
(F) TISSUE TYPE:
(G) CELL TYPE:
(H) CELL LINE:

(xi) SEQUENCE DESCRIPTION: SEQ ID NO:3:

```
TATCTGCAGC  ATCTCCTTTC  CAACCCAATT  TTCCTTTGTC  ACCAATAAAA  CTTTGCATAT   60
TTCTAGCCAT  TTCTCCAATG  GTACCAGCAC  TTTTAGAAAG  ACTTTCTAAT  CCCTGCGCTC  120
CTTTTTGAAT  CATAGTTTGA  GCTAATCTCG  TAGATGCAGA  TTTCTTTTCA  GATGCTGTTT  180
CACTTCCGCC  TGCACCCAGT  CCTATTGCAA  TGGCAGAGGC  AATAGAAGAA  GCATTGCTGA  240
TATTAAATTG  TTGGCCAATC  TTCTTACCTC  GATCAAGAAC  GTAAGATAAT  TTTCTACTTT  300
CAGCTGCATC  CAAACCCATT  CCGTAACCTT  CAGAGGCACT  TCTA                    344
```